United States Patent [19]

Denius, Jr.

[11] Patent Number: 4,610,511

[45] Date of Patent: Sep. 9, 1986

[54] ASSEMBLY AND METHOD FOR PRODUCING SPECIFIC OPTICAL INTERFERENCE PATTERNS

[76] Inventor: Homer R. Denius, Jr., P.O. Box 143, Big Horn, Wyo. 82833

[21] Appl. No.: 593,938

[22] Filed: Mar. 27, 1984

[51] Int. Cl.$^4$ .............................................. B44F 1/06
[52] U.S. Cl. .................................. 350/402; 350/404; 350/407
[58] Field of Search ....................... 350/402, 404, 407

[56] References Cited

U.S. PATENT DOCUMENTS

| | | | |
|---|---|---|---|
| 1,090,278 | 3/1914 | Coates | 350/286 |
| 2,305,777 | 12/1942 | Hansen et al. | 350/287 |
| 2,594,698 | 4/1952 | Thomas | 350/287 |
| 2,678,589 | 5/1954 | Erban | 350/286 |
| 2,966,005 | 12/1960 | Anderson | 350/286 |
| 3,120,720 | 2/1964 | Brudney | 350/286 |
| 3,535,025 | 10/1970 | Shannon | 350/286 |

*Primary Examiner*—Bruce Y. Arnold
*Attorney, Agent, or Firm*—Sheridan, Ross & McIntosh

[57] ABSTRACT

An assembly is provided which employs a light source that directs slightly convergent light rays of visual frequencies towards a first polarizing means. The first polarizing means polarizes the light rays and directs them towards a first lateral face of a transparent, pyramidal object, and/or towards a reflecting means which in turn directs the received light rays towards the base of said object. Said object must display birefractive properties, and must have at least four optical axes. Upon encountering said object, a portion of the light rays enter into said object and eventually, many of the light rays unite on any one of several optical paths that extend from a second lateral face and/or the base of the object in a convergent fashion. The united light rays create interferences on each of said optical paths. A combination of said converging optical paths creates an interference pattern. By viewing said second lateral face and/or base of the object via a second polarizing means, the interference pattern can be visually perceived. Depending on the specific arrangement of the components of the present invention, a viewer can visually perceive an interference pattern that resembles a two-eyed winged structure, a scarabus beetle, or a pharaoh's head.

18 Claims, 6 Drawing Figures

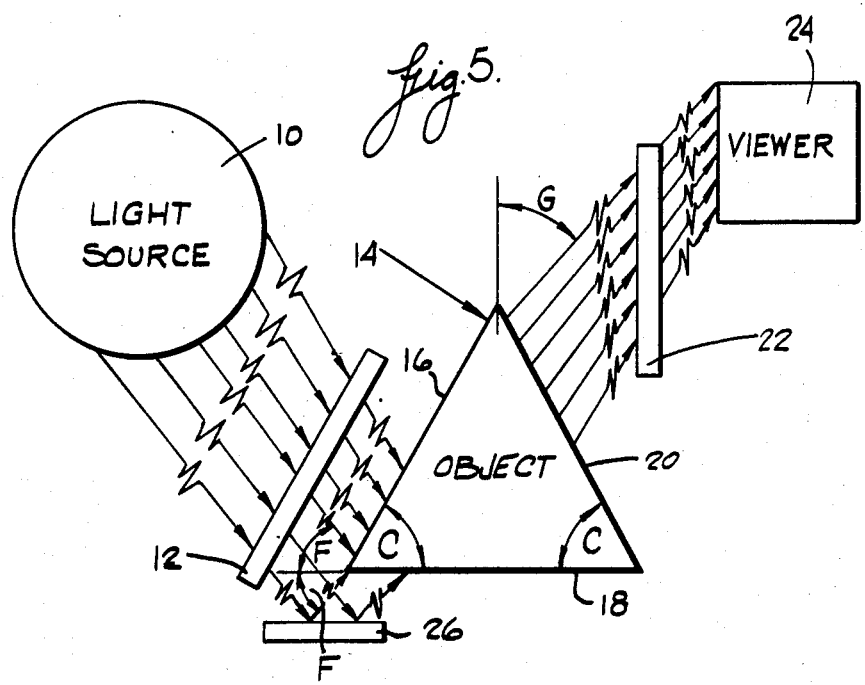
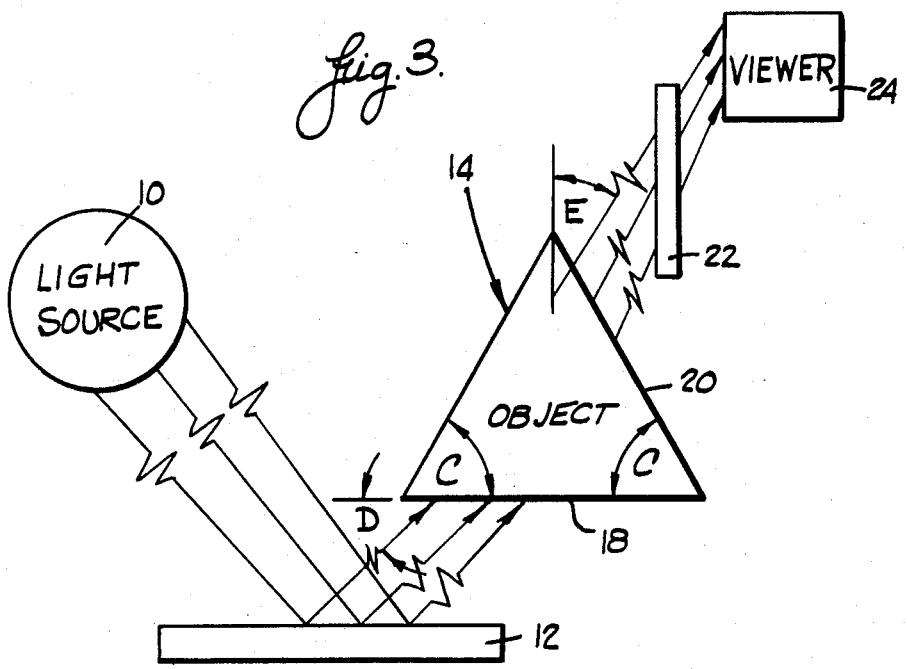

ASSEMBLY AND METHOD FOR PRODUCING SPECIFIC OPTICAL INTERFERENCE PATTERNS

FIELD OF THE INVENTION

The present invention relates to the production of light ray interference patterns, and in particular, to an assembly and method for producing specific optical interference patterns that are visually perceptible, and appear on one or more surfaces of a transparent, birefractive, pyramidal object.

BACKGROUND OF THE INVENTION

Many optical devices have been developed to act upon light rays to achieve a variety of desired results. Such inventions have frequently employed reflective and/or prismatic components to produce virtual images of real objects or to create a color spectrum through dispersive effects. In the operation of such prior art devices, planned optical interference of light rays to produce specific interference patterns has not played a role. It will become evident therefore, that the present invention is novel since it discloses an assembly and method for producing certain perceptible light ray interference patterns utilizing a transparent birefractive object.

The scientific phenomenon of perceptible light ray interference most typically occurs when convergent polarized light rays which have substantially the same frequency, but which are out-of-phase, are overlapped on a common optical path. In such instances, the light rays "destructively" interfere at some points to create dark bands, and "constructively" interfere at other points to create bright bands. The configuration of the dark and bright bands will depend upon the phase relationship between the interfering light rays. If the light that is utilized to create an interference is comprised of a plurality of light ray members of the visible light spectrum, (e.g. white light), the resultant interference pattern will be vividly colored.

When visually perceptible light ray interference is induced by passing light rays through a transparent, birefractive object, the phase relationship between the interfering light rays is dictated by the disparate lengths of the different optical paths that are followed by the interfering light rays before they are united on a common optical interference path. The optical path followed by a light ray traveling within a transparent, birefractive object is principally influenced by the orientation of the optical axes within the object, and the refractive index of the object. The orientation of the optical axes is dependent upon the crystalline structure of the object and/or internal stresses within the object, and the type of material comprising the object.

DISCLOSURE OF THE INVENTION

The present invention is directed to an assembly and method for producing three visually perceptible optical interference patterns. The assembly includes a light source which directs convergent light rays of visual frequencies towards a first polarizing means. When the light rays emerge from said polarizing means they are in a polarized state. The polarized light rays then encounter at least one surface of a transparent, birefractive object at an angle of incidence that allows at least a portion of the light rays to enter into the object. To produce the three desired interference patterns, the object must be in the shape of a pyramid, having a square base and four symmetrical, triangular-shaped lateral faces. In addition, the object must be composed of a material that displays birefractive properties when the material is properly molded into the above-specified, pyramidal shape. Due to the natural stresses induced by the molding process, the object should have at least four optical axes.

Upon entering into the object, each of the afore-mentioned convergent, polarized light rays is split into two independent light rays. Such splitting effect is due to the refractive properties of the object. All of the resultant light rays then travel through the object, and all, or a portion of each such resultant light ray passes out of the object, or is reflected internally upon encountering a surface of the object. Eventually, many of the light rays are united on one of several common optical paths that extend out of a single surface of the object in a convergent fashion. Since the light rays that are united on a single common optical path have followed different paths within the object before reaching the common optical path, the light rays of substantially common frequencies are out-of-phase and an interference is created. The combination of the interferences that are produced on all of the converging optical paths extending out of said single surface of the object creates an interference pattern.

A second polarizing means is provided so that the light rays that are emitted from the object on said converging optical paths are polarized. Such polarization allows for the visual perception of said interference pattern.

By properly positioning the light source, object, and first and second polarizing means, the present invention allows for the production and visual perception of three specific interference patterns. Said three interference patterns resemble a pharaoh's head, a scarabus beetle, and a two-eyed winged structure, as hereinafter depicted.

BRIEF DESCRIPTION OF THE DRAWINGS

FIG. 3 is a side elevation view of the components that comprise a second embodiment of the present invention, and which act together to produce an interference pattern that resembles a scarabus beetle.

FIG. 5 is a side elevation view of the components that comprise a third embodiment of the present invention, and which act together to produce an interference pattern that resembles a pharaoh's head.

DETAILED DESCRIPTION OF THE INVENTION

Figure 1:
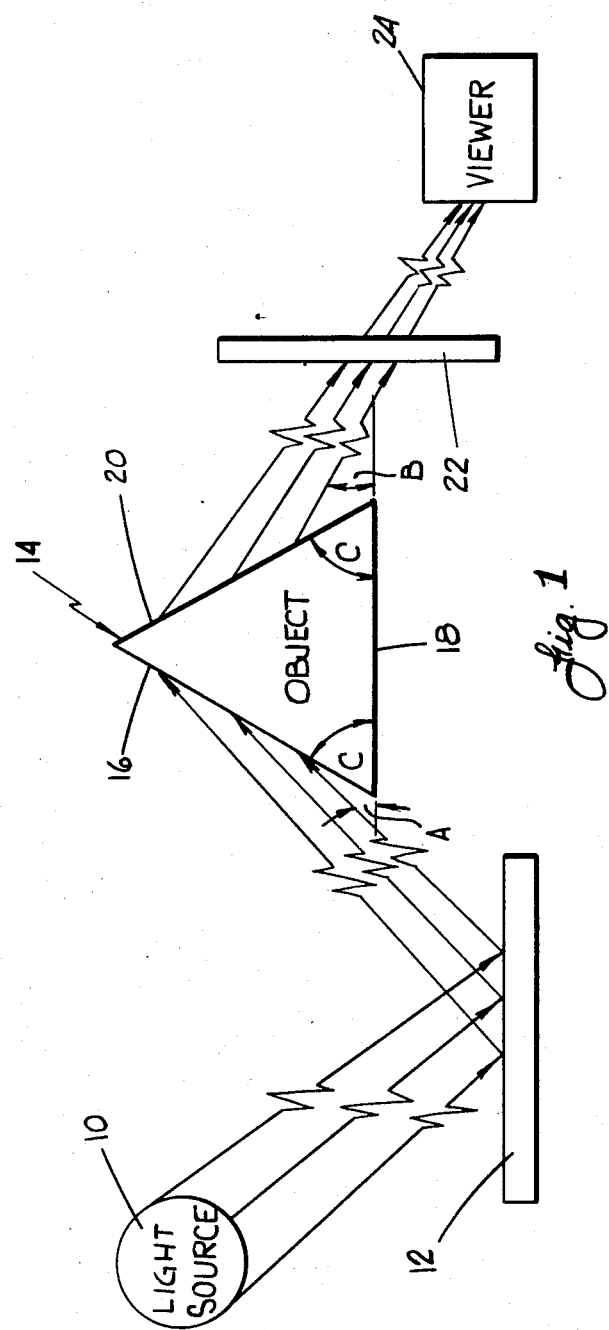
FIG. 1 is a side elevation view of the components that comprise a first embodiment of the present invention, and which act together to produce an interference pattern that resembles a two-eyed winged structure.

In accordance with a first embodiment of the present invention, FIG. 1 shows a side elevation view of the components that comprise the assembly. A light source 10 directs slightly convergent light rays of visual frequencies towards a first polarizing means 12. Said first polarizing means 12, as depicted in FIG. 1, may be a reflective surface, such as glass. It should be understood however, that the first polarizing means 12 may be any type of item, reflective or transparent, which can polarize light rays.

The first polarizing means 12 acts on said convergent light rays so as to both polarize them and direct them towards a first lateral face 16 of an object 14. The object 14 is shaped like a pyramid, having a square base 18 and four symmetrical, triangular-shaped lateral faces which each form an angle C with the base surface 18 of the object 14. By way of example, the angle C may equal approximately 52°. The object 14 must be transparent and birefractive, and must have at least four optical axes. By way of example, a standardized casting resin, (such as that sold under the trademark caroplastic), may be molded to form a pyramidal object 14 having the necessary attributes. caroplastic may be obtained from Carolina Biological Supply of Burlington, North Carolina.

The light source 10, first polarizing means 12, and object 14 are positioned so that the polarized light rays encounter said first lateral face 16 of the object 14, and form an average angle A relative to the plane defined by the base surface 18 of said object 14. The average angle A and the aforementioned angle C are coordinated so that a portion of each polarized light ray enters into the object 14 upon encountering said first lateral face 16. For a material such as caroplastic, which has a refractive index of about 1.56, an average angle A of approximately 36°, and an angle C of about 52° will suffice.

Each light ray that enters the object 14 is split into two independent rays. The resultant light rays then travel through the object 14 on different optical paths until eventually, many of the light rays unite on one of several optical paths that extend out of a second lateral face 20 of the object 14 in a slightly convergent fashion. Said second lateral face 20 is opposite to said first lateral face 16. Since the light rays that unite on said converging optical paths have followed different paths within the object 14 before reaching a common path, light rays of substantially common frequencies are out-of-phase and an interference is therefore created. The combination of the interferences that are produced on all of said converging optical paths extending out of the object 14, creates an interference pattern. To visually perceive said interference pattern, a viewer 24 must be positioned adjacent to said lateral face 20 of the object 14, with a second polarizing means 22 interposed therebetween. Said second polarizing means 22, as depicted in FIG. 1, may be a transparent item such as Polaroid sunglasses. It should be understood however, that the second polarizing means 22 may be any type of item, reflective or transparent, which can polarize light rays. Said viewer 24 may be a human being, or any device capable of visually perceiving light ray interference patterns.

Said viewer 24 and second polarizing means 22 are positioned so that they lie on the optical path of those converging light rays which extend from said object 14 at an approximate angle B, relative to the base surface 18 of the object 14. When the object 14 is made of caroplastic; said average angle A equals 36°; and said angle C equals 52°; an approximate angle B of 36° ensures optimal viewing of said interference pattern by the viewer 24.

Figure 2:
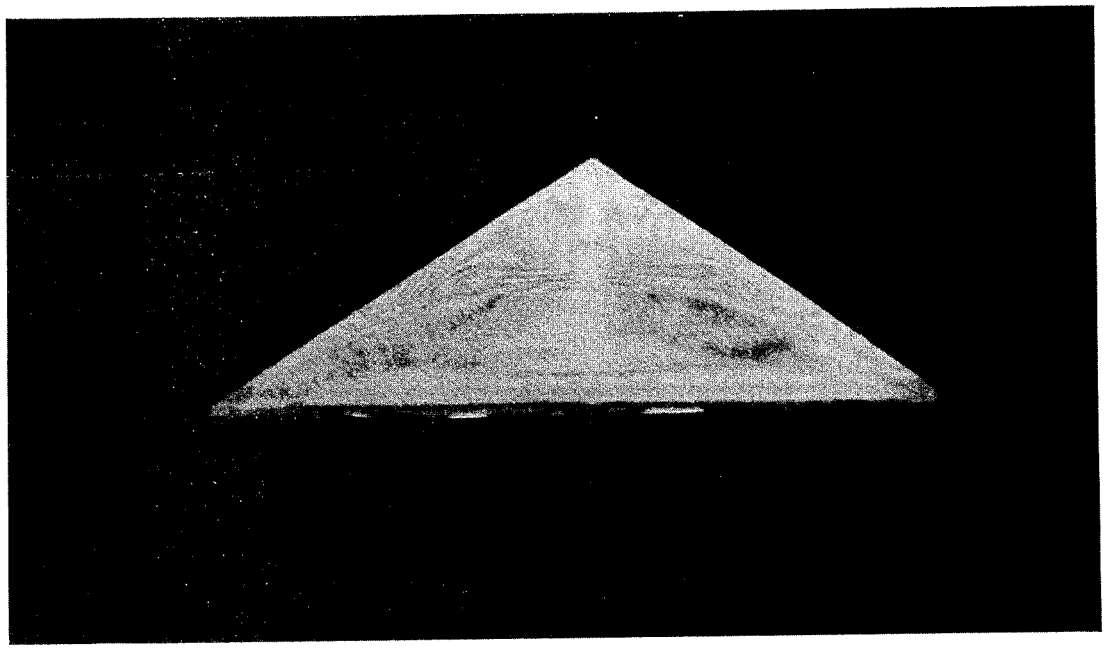
FIG. 2 is a photographic illustration of the two-eyed winged structure interference pattern that can be visually perceived when the present invention is arranged in the manner of said first embodiment.

By viewing said second lateral face 20 of the object 14 via the second polarizing means 22 the viewer 24 is able to visually perceive said interference pattern, and said pattern will resemble a two-eyed winged structure. The interference pattern will appear as though it is on said second lateral surface 20 of the object 14. FIG. 2 is a photograph which illustrates, in a general manner, the configuration of the two-eyed winged structure which a viewer 24 is able to visually perceive.

FIG. 3 shows a side elevation view of the components that comprise the assembly of a second embodiment of the present invention. It should be apparent, that said components are the same as those described with regard to the first embodiment. The operation of the second embodiment is also quite similar to the operation of said first embodiment.

In accordance with the second embodiment, a light source 10 directs slightly convergent light rays of visual frequencies towards a first polarizing means 12. Said light source 10 could for example be a surface that reflects light from another light source. Upon receiving the light rays, the first polarizing means polarizes the rays then directs the rays towards the base surface 18 of an object 14. The object 14 must have the same shape and other characteristics as specified above with regard to the pyramidal object included in the first embodiment. As previously indicated, an object 14 composed of caroplastic will display the necessary attributes.

The light source 10, first polarizing means 12, and object 14 are positioned so that the polarized light rays encounter said base surface 18 of the object 14, and form an average angle D, relative to the plane defined by the base surface 18. The average angle D, and the angle C formed by the base surface 18 and each of the lateral faces of the object 14, are coordinated so that a portion of each polarized light ray enters into the object 14 upon encountering said base surface 18. For a material such as caroplstic which has a refractive index of about 1.56, an average angle D of approximately 16°, and an angle C of about 52°, will suffice.

Each of the light rays that enters into the object 14 is split into two independent rays. The resultant light rays then travel through the object 14 on different optical paths until eventually, many of the light rays unite on one of several optical paths that extend out of a lateral face 20 of the object 14 in a slightly convergent fashion. Since the light rays that unite on said converging optical paths have followed different paths within the object 14 before reaching a common path, light rays of substantially common frequencies are out-of-phase and an interference is therefore created. The combination of the interferences that are produced on all of said converging optical paths extending out of the object 14, creates an interference pattern. To visually perceive said interference pattern, a viewer 24 must be positioned adjacent to said lateral face 20 of the object 14, with a second polarizing means 22 interposed therebetween. Said viewer 24 and second polarizing means 22 are positioned so that they lie on the optical path of those converging light rays which extend from said object 14 at an approximate angle E, relative to the longitudinal center axis of the object 14. When the object is made of caroplastic; said average angle D equals 16°; and said angle C equals 52°; an approximate angle E of 29° ensures optimal viewing of said interference pattern by the viewer 24.

Figure 4:
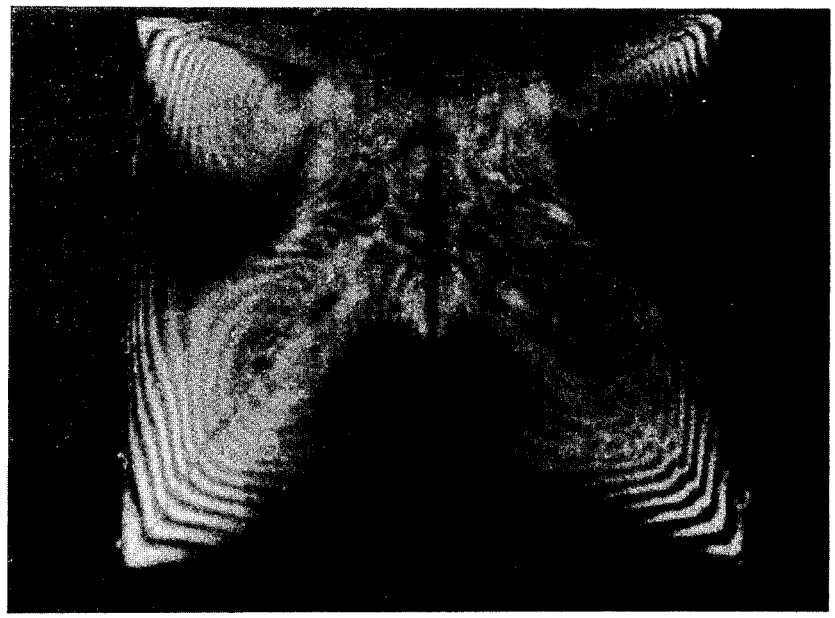
FIG. 4 is a photographic illustration of the scarabus beetle interference pattern that can be visually perceived when the present invention is arranged in the manner of said second embodiment.

By viewing said lateral face 20 of the object 14 via the second polarizing means 22 the viewer 24 is able to visually perceive said interference pattern, and said pattern will resemble a scarabus beetle. The interference pattern will appear as though it is on said lateral face 20 of the object 14. FIG. 4 is a photograph which illustrates, in a general manner, the configuration of the scarabus beetle interference pattern which a viewer 24 is able to visually perceive.

It should be noted that the positions of the light source 10 and viewer 24 in the second embodiment can be interchanged so that the light rays enter said lateral surface 20 at an average angle E; and the converging optical interference paths extend out of the base surface 18 at an average angle D. With that arrangement, said scarabus beetle interference pattern can be visually perceived by viewing the base surface 18 of the object 14 via the first polarizing means 12.

In accordance with a third embodiment of the present invention, FIG. 5 shows a side elevation view of the components that comprise the assembly. It should be apparent that said components are substantially the same as those set forth with regard to the first and second embodiments. The operation of the third embodiment is also similar to the operation of said first and second embodiments.

As shown in FIG. 5, a light source 10 directs slightly convergent light rays of visual frequencies towards a first polarizing means 12. Upon receiving said light rays, the first polarizing means 12 polarizes the rays, and allows a first portion of the rays to pass onward towards a first lateral face 16 of an object 14, while the remaining second portion of rays encounter a reflective means 26. The reflective means 26 may be any type of item capable of reflecting light rays, (e.g. a mirror). Upon receiving the second portion of light rays, the reflecting means 26 directs the light rays towards a base surface 18 of said object 14. The object 14 must have the same shape and other characteristics as specified above with regard to the pyramidal object included in the first embodiment. As previously indicated, an object 14 composed of caroplastic will display the necessary characteristics.

The light source 10, first polarizing means 12, reflecting means 26, and object 14 are positioned so that the polarized light rays encounter said first lateral face 16 and base surface 18 of the object 14, and form an average angle F relative to the plane defined by the base surface 18. The average angle F, and the angle C formed by the base surface 18 and each of the lateral faces of the object 14, are coordinated so that a portion of the polarized light rays enter into the object 14 upon encountering said base surface 18 and said first lateral face 16. For a material such as caroplastic, which has a refractive index of about 1.56, an average angle F of approximately 43°, and an angle C of about 52°, will suffice.

Each of the light rays that enters into the object 14 is split into two independent rays. The resultant light rays then travel through the object 14 on different optical paths until eventually, many of the light rays unite on one of several optical paths that extend out of a second lateral face 20 of the object 14 in a slightly convergent fashion. Said second lateral face 20 is opposite to said first lateral face 16. Since the light rays that unite on said converging optical paths have followed different paths within the object 14 before reaching a common path, light rays of substantially common frequencies are out-of-phase and an interference is created. The combination of the interferences that are produced on all of said converging optical paths that extend out of the object 14, creates an interference pattern. To visually perceive said interference pattern, a viewer 24 must be positioned adjacent to said second lateral face 20, with a second polarizing means 22 interposed therebetween. Said viewer 24 and second polarizing means 22 are positioned so that they lie on the optical path of those converging light rays which extend from said object 14 at an approximate angle G, relative to the longitudinal center axis of the object 14. When the object 14 is made of caroplastic; said average angle F equals 43°; and said angle C equals 52°; an approximate angle G of 47° ensures optimal viewing of said interference pattern by the viewer 24.

Figure 6:
FIG. 6 is a photographic illustration of the pharaoh's head interference pattern that can be visually perceived when the present invention is arranged in the manner of said third embodiment.

By viewing said second lateral face of the object 14 via the second polarizing means 22 the viewer 24 is able to visually perceive said interference pattern, and said pattern will resemble an upside down pharaoh's head. The pharaoh's head interference pattern will appear as though it is on said second lateral face 20 of the object 14. FIG. 6 is a photograph which illustrates, in a general manner, the inverted configuration of the pharaoh's head interference pattern which a viewer 24 is able to visually perceive.

Based on the above detailed description, salient features of the present invention can be easily recognized. Each of the three disclosed embodiments employs a light source that directs slightly convergent light rays of a visual frequency towards a first polarizing means. The first polarizing means polarizes the light rays and directs them towards a first lateral face of a transparent, pyramidal object, and/or towards a reflecting means which in turn directs the received light rays towards the base of said object. Said object must display birefractive properties, and must have at least four optical axes. Upon encountering said object, a portion of the light rays enter into said object and eventually, many of the light rays unite on any one of several optical paths that extend from a second lateral face and/or the base of the object in a convergent fashion. The united light rays create interferences on each of said optical paths. A combination of said converging optical paths creates an interference pattern. By viewing said second lateral face and/or base of the object via a second polarizing means, the interference pattern can be visually perceived. Depending on the specific arrangement of the components of the present invention, a viewer can visually perceive an interference pattern that resembles a two-eyed winged structure, a scarabus beetle, or a pharaoh's head.

Although the present invention has been described with reference to three particular embodiments, it is readily understood that certain variations and modifications could be effected within the spirit and scope of this invention.

What is claimed is:

1. An assembly for producing a visually perceptible light ray interference pattern, comprising:
    (a) a means for providing light rays of visual frequencies;
    (b) a first means for polarizing said light rays;
    (c) a pyramidal shaped object having a square base and four symmetrical, triangular-shaped lateral faces, said object being composed of a transparent, birefractive material, and having at least four optical axes; and wherein said object internally receives a portion of said polarized light rays, organizes a portion of said received light rays into an interference pattern, and emits externally said organized light rays on converging optical paths; and (d) a second means for polarizing said emitted light rays so that said interference pattern can be visually perceived by viewing said object along said converging optical paths via the second polarizing means.

2. An assembly, as recited in claim 1, wherein said object receives said portion of polarized light rays through a first lateral face, and emits said organized light rays through a second lateral face that is opposite to said first lateral face, and wherein said interference pattern resembles a two-eyed winged structure.

3. An assembly, as recited in claim 2, wherein:
(a) said portion of polarized light rays received by said object encounter said object at an average angle of 36°, relative to the plane defined by said base of said object;
(b) said object is composed of caroplastic;
(c) each said lateral face of said object forms a 52° angle with said base of said object, relative to the plane defined by said base of said object; and
(d) said converging optical paths form an average angle of 36°, relative to the plane defined by said base of said object.

4. An assembly, as recited in claim 1, wherein said object receives said portion of polarized light rays through said base, and emits said organized light rays through one of said lateral faces, and wherein said interference pattern resembles a scarabus beetle.

5. An assembly, as recited in claim 4, wherein
(a) said portion of polarized light rays received by said object encounter said object at an average angle of 16°, relative to the plane defined by the base of said object;
(b) said object is composed of caroplastic;
(c) each said lateral face of said object forms a 52° angle with said base of said object, relative to the plane defined by said base of said object; and
(d) said converging optical paths form an average angle of 29°, relative to the longitudinal center axis of said object.

6. An assembly, as recited in claim 1, wherein said object receives said portion of polarized light rays through one of said lateral faces, and emits said organized light rays through said base, and wherein said interference pattern resembles a scarabus beetle.

7. An assembly as recited in claim 6, wherein:
(a) said portion of polarized rays received by said object encounter said object at an average angle of 29°, relative to the longitudinal center axis of said object;
(b) said object is composed of caroplastic;
(c) each said lateral face of said object forms a 52° angle with said base of said object, relative to the plane defined by said base of said object; and
(d) said converging optical paths form an average angle of 16°, relative to the plane defined by the base of said object.

8. An assembly, as recited in claim 1, wherein said object receives said portion of polarized light rays through said base and a first lateral face, and emits, said organized light rays through a second lateral face that is opposite to said first lateral face, and wherein said interference pattern resembles a pharaoh's head.

9. An assembly as recited in claim 8, wherein:
(a) said portion of polarized light rays received by said object encounter said object at an average angle of 43°, relative to the plane defined by the base of said object;
(b) said object is composed of caroplastic;
(c) each said lateral face of said object forms a 52° angle with said base of said object, relative to the plane defined by said base of said object; and
(d) said converging optical paths form an average angle of 47°, relative to the longitudinal center axis of said object.

10. A method for producing a visually perceptible light ray interference pattern, comprising the steps of:
(a) providing light rays of visual frequencies;
(b) polarizing said light rays;
(c) receiving a portion of said polarized light rays in a transparent, birefractive, pyramidal object having a square base and four symmetrical, triangular-shaped lateral faces, and having at least four optical axes;
(d) organizing within said object, a portion of said received light rays into an interference pattern;
(e) emitting from said object, said organized light rays on converging optical paths; and
(f) polarizing said emitted light rays so that said interference pattern may be visually perceived by viewing said object along said converging optical paths.

11. A method, as recited in claim 10, wherein said receiving step includes receiving said portion of polarized light rays through a first lateral face of said object, wherein said emitting step includes emitting said organized light rays through a second lateral face of said object, and wherein said interference pattern resembles a two-eyed winged structure.

12. A method, as recited in claim 11, wherein:
(a) said portion of polarized light rays received by said object encounter said object at an average angle of 36°, relative to the plane defined by said base of said object;
(b) said object is composed of caroplastic;
(c) each said lateral face of said object forms a 52° angle with said base of said object, relative to the plane defined by said base of said object; and
(d) said converging optical paths form an average angle of 36°, relative to the plane defined by said base of said object.

13. A method, as recited in claim 10, wherein said receiving step includes receiving said portion of polarized light rays through said base of said object, wherein said emitting step includes emitting said, organized light rays through one of said lateral faces of said object, and wherein said interference pattern resembles a scarabus beetle.

14. A method, as recited in claim 13, wherein:
(a) said portion of polarized light rays received by said object encounter said object at an average angle of 16°, relative to the plane defined by the base of said object;
(b) said object is composed of caroplastic;
(c) each said lateral face of said object forms a 52° angle with said base of said object, relative to the plane defined by said base of said object; and
(d) said converging optical paths form an average angle of 29°, relative to the longitudinal center axis of said object.

15. A method as recited in claim 10, wherein said receiving step includes receiving said portion of polarized light rays through one of said lateral faces of said object, wherein said emitting step includes emitting said organized light rays through said base of said object, and wherein said interference pattern resembles a scarabus beetle.

16. A method, as recited in claim 15, wherein:
 (a) said portion of polarized light rays received by said object encounter said object at an average angle of 29°, relative to the longitudinal center axis of said object;
 (b) said object is composed of caroplastic;
 (c) each said lateral face of said object forms a 52° angle with said base of said object, relative to the plane defined by said base of said object; and
 (d) said converging optical paths form an average angle of 16°, relative to the plane defined by the base of said object.

17. A method, as recited in claim 10, wherein said receiving step includes receiving said portion of polarized light rays through a first lateral face and said base of said object, wherein said emitting step includes emitting said organized light rays through a second lateral face of said object that is opposite to said first lateral face of the object, and wherein said interference pattern resembles a pharaoh's head.

18. A method, as recited in claim 17, wherein:
 (a) said portion of polarized light rays received by said object encounter said object at an average angle of 43°, relative to the plane defined by the base of said object;
 (b) said object is composed of caroplastic;
 (c) each said lateral face of said object forms a 52° angle with said base of said object, relative to the plane defined by said base of said object; and
 (d) said converging optical paths form an average angle of 47°, relative to the longitudinal center axis of said object.

* * * * *